United States Patent
Chioini et al.

(10) Patent No.: US 11,517,555 B2
(45) Date of Patent: Dec. 6, 2022

(54) SOLID SOLUBLE FERRIC PYROPHOSPHATE FORMULATIONS, KITS, AND METHODS USING THE SAME

(71) Applicant: ROCKWELL MEDICAL, INC., Wixom, MI (US)

(72) Inventors: Robert Chioini, Wixom, MI (US); Ajay Gupta, Las Vegas, NV (US)

(73) Assignee: Rockwell Medical, Inc., Wixom, MI (US)

( * ) Notice: Subject to any disclaimer, the term of this patent is extended or adjusted under 35 U.S.C. 154(b) by 0 days.

(21) Appl. No.: 15/756,286

(22) PCT Filed: Sep. 2, 2016

(86) PCT No.: PCT/US2016/050120
§ 371 (c)(1),
(2) Date: Feb. 28, 2018

(87) PCT Pub. No.: WO2017/040937
PCT Pub. Date: Mar. 9, 2017

(65) Prior Publication Data
US 2018/0243256 A1  Aug. 30, 2018

Related U.S. Application Data

(60) Provisional application No. 62/214,908, filed on Sep. 4, 2015.

(51) Int. Cl.
| | | |
|---|---|---|
| A61K 31/295 | (2006.01) | |
| A61K 9/16 | (2006.01) | |
| A61M 1/16 | (2006.01) | |
| A61M 1/28 | (2006.01) | |

(52) U.S. Cl.
CPC .......... *A61K 31/295* (2013.01); *A61K 9/1611* (2013.01); *A61K 9/1623* (2013.01); *A61K 9/1688* (2013.01); *A61M 1/1666* (2014.02); *A61M 1/287* (2013.01); *A61M 2202/064* (2013.01)

(58) Field of Classification Search
CPC .. A61K 31/295; A61K 9/1611; A61K 9/1623; A61K 9/1688; A61M 1/1666; A61M 1/287; A61M 2202/064; A61P 7/06; A61P 7/08
USPC ......................................................... 514/402
See application file for complete search history.

(56) References Cited

U.S. PATENT DOCUMENTS

| | | | | |
|---|---|---|---|---|
| 5,177,068 | A * | 1/1993 | Callingham | C07D 213/69 514/184 |
| 6,395,180 | B2 * | 5/2002 | Chioini | B01F 15/00155 137/88 |
| 6,682,761 | B2 * | 1/2004 | Pace | A61K 9/145 424/489 |
| 6,689,275 | B1 | 2/2004 | Gupta | |
| 6,779,468 | B1 | 8/2004 | Gupta | |
| 6,974,593 | B2 * | 12/2005 | Henriksen | A61K 9/14 424/490 |
| 7,754,243 | B2 * | 7/2010 | Sun | A61K 9/10 424/489 |
| 7,816,404 | B2 * | 10/2010 | McCall, Jr. | A61K 31/194 424/646 |
| 7,857,977 | B2 | 12/2010 | Wash | |
| 8,178,709 | B2 * | 5/2012 | Nelson | A61K 31/194 556/17 |
| 2001/0042717 | A1 * | 11/2001 | Chioini | B01F 15/00155 210/646 |
| 2004/0052854 | A1 | 3/2004 | Yoshinari et al. | |
| 2006/0134227 | A1 * | 6/2006 | Bortz | A61K 31/19 424/646 |
| 2007/0012622 | A1 * | 1/2007 | Wash | A61K 33/26 210/647 |
| 2009/0023686 | A1 * | 1/2009 | McCall, Jr. | A61K 31/194 514/106 |
| 2009/0028962 | A1 * | 1/2009 | Bortz | A61K 31/19 424/646 |
| 2009/0061068 | A1 * | 3/2009 | Marshman | A23L 33/165 426/648 |
| 2012/0177700 | A1 * | 7/2012 | Imran | A61K 9/14 424/400 |
| 2015/0366907 | A1 | 12/2015 | Gupta | |

FOREIGN PATENT DOCUMENTS

| | | |
|---|---|---|
| JP | 2000-007557 A | 1/2000 |
| WO | 2012092305 A2 | 7/2012 |

OTHER PUBLICATIONS

Rossi et al. (Food Chemistry 151 (2014) 243-247).*
Rita Wegmuller et al. (J. Nutr. 134: 3301-3304, 2004, Particle Size Reduction and Encapsulation Affect the Bioavailability of Ferric Pyrophosphate in Rats).*
The International Search Report for PCT/US2016/050120, 3 pages, dated Nov. 23, 2016.
Eschbach, J. W. et al., "Iron balance in hemodialysis patients." Annal. Int. Med. 87:710-713 (1977).
Shah, R. B. et al., "Comparative evaluation of flow for pharmaceutical powders and granules." AAPS PharmSciTech 9 (1): 250-258 (2008).
Gupta, A. et al., "Ferric pyrophosphate citrate administered via dialysate reduces erythropoiesis-stimulating agent use and maintains hemoglobin in hemodialysis patients." Kidney Int. 88(5): 1187-1197 (2015).

(Continued)

*Primary Examiner* — Sabiha N Qazi
(74) *Attorney, Agent, or Firm* — McDonnell Boehnen Hulbert & Bergthoff LLP

(57) ABSTRACT

A solid particulate formulation comprising soluble ferric pyrophosphate and a sachet comprising the solid particulate formulation of soluble ferric pyrophosphate for adding to a dialysis solution are provided. Improved methods of administering soluble ferric pyrophosphate comprising the solid particulate formulations and kits comprising the solid particulate formulation and a dialysis concentrate formulation are also disclosed.

24 Claims, No Drawings

(56) References Cited

OTHER PUBLICATIONS

Fishbane, S. N. et al., "Ferric pyrophosphate citrate (Triferic(TM)) administration via the dialysate maintains hemoglobin and iron balance in chronic hemodialysis patients." Nephrol. Dial. Transplant 30:2019-2026 (2015).
Shulan, L., "Biopharmacetuics and Pharmacodynamics," p. 25.
Ruhua, Z., "II. Fluidity of Powders," Industrial Pharmaceutics, pp. 83-84.
Shin yakuzai galu (New pharmacoloy), Dec. 15, 2011, pp. 316, 326, and 327.
Campos, M. et al., "A Comparative Analysis of the Flow Properties between Two Alumina-Based Dry powder." Adv. Mater. Sci. Eng. Art. ID 519846, 2013.
Shi H. et al., "Granular Flow: From Dilute to Jammed States," In: Sakellariou, M. (Ed.), Granular Materials, p. 43-67, 2017.
Munroe, R. "What Makes Sand Fot?" The New York Times, Nov. 9, 2020.

\* cited by examiner

SOLID SOLUBLE FERRIC PYROPHOSPHATE FORMULATIONS, KITS, AND METHODS USING THE SAME

CROSS-REFERENCE TO RELATED APPLICATION

The benefit under 35 U.S.C. § 119(e) of U.S. Provisional Patent Application No. 62/214,908, filed Sep. 4, 2015, is hereby claimed, and the disclosure thereof is incorporated herein by reference.

FIELD OF INVENTION

The present disclosure relates to a solid particulate formulation comprising soluble ferric pyrophosphate that can be mixed with dialysis solution to form a dialysate and administered to patients.

BACKGROUND

Iron deficiency is the most common micronutrient deficiency in the world. Iron has several vital physiological functions, including: (1) carrier of oxygen from lung to tissues; (2) transporter of electrons within cells; and (3) co-factor of essential enzymatic reactions in neurotransmission, synthesis of steroid hormones, synthesis of bile salts, and detoxification processes in the liver. Severe iron deficiency, i.e., iron deficiency anemia, is therefore particularly debilitating. Among the consequences of iron deficiency anemia are increased maternal and fetal mortality, an increased risk of premature delivery and low birth weight, learning disabilities and delayed psychomotor development, reduced work capacity, impaired immunity (high risk of infection), an inability to maintain body temperature, and an associated risk of lead poisoning.

Iron deficiency anemia commonly affects patients having chronic diseases, such as kidney disease, inflammatory bowel disease, cancer, HIV, and diabetes. For example, patients receiving regular dialysis treatments for chronic renal failure very frequently are also afflicted with anemia. Dialysis is a procedure for removing waste products from the blood of a patient when the kidneys are unable to do so on their own, for example, patients with chronic renal failure. Hemodialysis is a form of dialysis in which waste products are removed from the blood by passing the blood along one side of a semi-permeable membrane and passing a specially formulated dialysis solution (i.e., dialysate) along the other side of the semi-permeable membrane. The waste materials that are to be removed from the blood pass with the help of diffusion from the blood of the patient to the dialysis solution through the permeable membrane. Hemodiafiltration is another method for removing waste products from blood, wherein waste products are removed by convection and dialysate is infused into the patient as a replacement fluid.

The dialysate is an aqueous solution containing various electrolytes. The dialysate generally comprises dissolved sodium chloride, potassium chloride, calcium chloride, acetate ions, dextrose and other constituents, in about the same concentration as normal plasma. Urea, creatinine, uric acid, phosphate and other metabolites normally eliminated by the kidneys diffuse from the blood of the patient into the dialysate until equivalent concentrations of the compounds are in the blood and dialysate. The volume of dialysate fluid used is much greater than the blood volume. The great disparity in volume and the replenishment of dialysate with fresh dialysate ensure that metabolites and excess electrolytes are removed almost completely from the blood.

The dialysate is generally prepared from a dialysis concentrate formulation, which contains, for example, sodium ions, potassium ions, calcium ions, magnesium ions, chloride ions, acetate ions, citrate, and dextrose; a bicarbonate solution; and water. The dialysis concentrate, bicarbonate solution and water are generally combined at, or in close proximity to, the dialysis machine.

It is well known that it is very difficult to treat an iron deficiency with orally administered iron supplements. In general, relatively large doses are needed to achieve a desired therapeutic effect. Oral administration of iron supplements is known to be commonly accompanied by undesirable side effects including nausea, vomiting, constipation and gastric irritation. To overcome the problems associated with oral delivery of iron, a great deal of effort has been directed to developing iron-containing formulations that are suitable for parenteral administration. Parenterally administered formulations are, in general, aqueous solutions of specific formulation components, in which the solution pH is in the range from pH 4 to pH 8. Parenteral administration encompasses administration by intravenous injection, intramuscular injection, or dialysis.

The formulation of iron-containing compositions for parenteral administration is particularly difficult. The solubility of iron compounds in water is strongly dependent on the pH of the solution and the presence of other formulation components. In general, iron salts are soluble in acidic solutions. Conversely, in basic solutions, iron ions will form insoluble oxides and precipitate from the formulation, unless a chelating agent, such as EDTA is present.

Soluble ferric pyrophosphate (SFP) is a complex iron salt that has a molecular mass of about 1000 Da and is highly soluble in aqueous solutions, allowing its infusion via aqueous solutions, e.g., dialysate. The administration of SFP overcomes both absolute and functional iron deficiencies in patients, including hemodialysis-dependent CKD (HDD-CKD) patients, and could significantly reduce the amount of erythropoiesis-stimulating agents needed to treat these patients.

U.S. Pat. Nos. 6,689,275; 6,779,468; and 7,857,977; incorporated herein by reference, disclose the addition of SFP to liquid bicarbonate solutions for hemodialysis. However, conventional SFP compositions, such as food grade SFP (FCC-SFP), can dissolve incompletely in aqueous solutions and are not suitable for pharmaceutical applications.

SUMMARY OF INVENTION

The present disclosure is directed to a solid particulate formulation of soluble ferric pyrophosphate (SFP). In one aspect, the solid particulate formulation of SFP is a powder formulation. In another aspect, the solid particulate formulation of SFP is a granule formulation. In one aspect, the dialysis concentrate formulation is an acid. In another aspect, the dialysis concentrate formulation is a base. The present disclosure further provides a kit comprising a solid particulate formulation of SFP and a dialysis concentrate formulation in a solid or liquid form.

The present disclosure provides a solid particulate formulation of SFP comprising SFP having a particle size less than about 5 microns, wherein the SFP dissolves in aqueous solution, e.g., dialysis solution or intravenous solution or intravenous fluids, in less than 1 minute. In one aspect, the solubility of the SFP in aqueous solution is greater than 1 gram per milliliter. In one aspect, the SFP has an angle of repose less than 45 degrees, optionally less than 42 degrees. In another aspect, the solid particulate formulation is stable in aqueous solution at ambient temperature for at least 24 months.

In one aspect, the solid particulate formulation of SFP comprises SFP comprising iron chelated with citrate and pyrophosphate. In one aspect, the SFP comprising iron chelated with citrate and pyrophosphate is ferric pyrophosphate citrate (FPC) having structure (I):

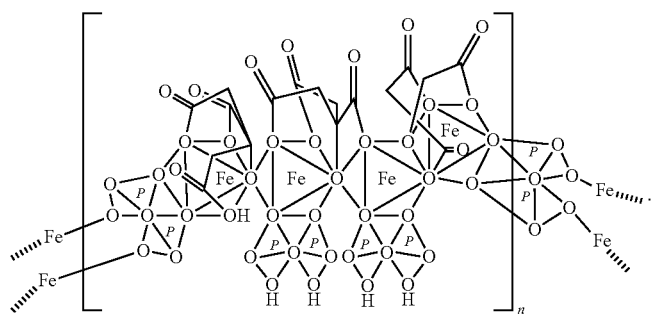

(I)

In one aspect, the solid particulate formulation comprises SFP comprising iron in an amount of 7% to 11% by weight, citrate in an amount of at least 14% by weight, and pyrophosphate in an amount of at least 10% by weight.

The present disclosure also provides a sachet (e.g., a packet) comprising a solid particulate formulation of SFP described herein. In one aspect, the sachet comprises a dose or multiple doses of SFP that will be added to a dialysis solution to form a dialysate and result in a final iron concentration of about 110 mcg/L (about 2 µM) in the dialysate to be administered to a patient e.g., during hemodialysis or hemodiafiltration. In another aspect, the sachet comprises a dose or multiple doses of SFP that will be added to an intravenous solution to form an intravenous fluid with a final iron concentration of 1 mg per liter to 1 mg per mL, to be administered to a patient via intravenous injection or infusion. In another aspect, the sachet comprises a dose or multiple doses of SFP that can be mixed with food or drink to provide a nutritional supplement.

The present disclosure further provides an improved method of administering SFP comprising (a) mixing a solid particulate formulation of SFP with a dialysis solution to form a dialysate and (b) administering the dialysate to a subject in need. In one aspect, the dialysis solution is an acid solution. In one aspect, the acid solution comprises citrate or lactate. In another aspect, the dialysis solution is a base solution. In one aspect, the base solution comprises bicarbonate. In a further aspect, the solubility of the solid particulate formulation in the base solution is greater than 1 gram per mL. In one aspect, the mixing of the solid particulate formulation of SFP with the dialysis solution results in an iron concentration of about 100 mcg per L to about 150 mcg per L in the dialysate.

In one aspect, the improved method of administering SFP comprises administering a solid particulate formulation of SFP comprising iron chelated with citrate and pyrophosphate. In one aspect, the improved method of administering SFP comprises administering a solid particulate formulation of SFP comprising iron in an amount of 7% to 11% by weight, citrate in an amount of at least 14% by weight, and pyrophosphate in an amount of at least 10% by weight. In another aspect, the improved method of administering SFP comprises administering a solid particulate formulation of FPC comprising iron chelated with citrate and pyrophosphate having structure (I).

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure

DETAILED DESCRIPTION

The present disclosure provides a solid particulate formulation of soluble ferric pyrophosphate (SFP) and a kit comprising a solid particulate formulation of SFP and a dialysis concentrate formulation. The disclosure also provides an improved method of administering SFP comprising mixing a solid particulate formulation of SFP described herein with a dialysis solution to form a dialysate and administering the dialysate to a subject in need. The solid particulate formulation of SFP described herein and methods of using the same are superior to conventional forms of SFP.

The solid particulate formulation according to the present disclosure dissolves rapidly and completely in aqueous solutions and thus can be added directly to a dialysis concentrate formulation, e.g., a liquid bicarbonate concentrate, or a dialysate formulation. The solid particulate formulation thus provides many advantages compared to a liquid concentrate formulation of SFP. The solid particulate formulation does not need to be sterile, whereas the liquid concentrate formulation must be kept sterile because microbial growth is possible in a liquid formulation, but not in a solid particulate formulation. The solid particulate formulation of the present disclosure can be packaged in a sachet and the flowability characteristics of the solid particulate formulation allow for ease of addition by opening the sachet and allowing the solid particulate formulation to simply flow completely into the dialysis concentrate, with very little or no residual SFP remaining in the sachet. The solid particulate formulation also minimizes the volume and weight of packaging compared to a liquid formulation, resulting in less required storage space at the manufacturing site, during transport, at the distribution site and at the final site of use (e.g., a dialysis center).

As used herein, the following definitions may be useful in aiding the skilled practitioner in understanding the disclosure. Unless otherwise defined herein, scientific and technical terms used in the present disclosure shall have the meanings that are commonly understood by those of ordinary skill in the art.

Dialysis Precursors and Solutions

The term "dialysis" refers to the movement of solute and water through a semipermeable membrane (the dialyzer) which separates a solution to be filtered, e.g., blood, from a cleansing solution (the dialysate). Dialysis is a clinical treatment procedure by which metabolic by-products, toxins, and excess fluid are removed from the blood of a patient by transfer across a dialysis membrane. Dialysis includes hemodialysis, in which a synthetic membrane constitutes the dialysis membrane, and peritoneal dialysis, in which a patient's peritoneal membrane constitutes the dialysis membrane.

The terms "dialysate solution" and "dialysate" refer to the solution on the opposite side of the dialysis membrane from the patient's blood during dialysis or diafiltration. Hemodialysate is generally prepared from two dry powder concentrates, including acid ("A") and base ("B") concentrates, which are reconstituted in treated water before use, or from two aqueous concentrates. The A concentrate, containing an organic acid and electrolytes and osmotic agents other than bicarbonate, is mixed with the B concentrate containing bicarbonate and treated water in a dialysis machine to make the final hemodialysate. Presently, hemodialysis machines utilize an automated proportioning system to mix salts in deionized water in specific proportions to generate the final dialysate solution. The dialysate concentrates are usually supplied by the manufacturer either as a liquid solution ready to use or as a premixed powder that is added to purified water in large reservoirs. The concentrates are pumped into a chamber in the dialysis machine, where they are mixed with purified water to make the final dialysate solution.

The methods of the present disclosure may be used to treat patients undergoing dialysis, such as hemodialysis, or diafiltration, such as hemodiafiltration. Hemodialysis uses a hemodialyzer to remove certain solutes from blood by virtue of their concentration gradients across a semipermeable membrane. The hemodialyzer, also referred to as an artificial kidney, is an apparatus by which hemodialysis is performed, blood being separated by the semipermeable membrane from a solution of such composition as to secure diffusion of certain solutes from the blood. The hemodialyzer can be used for ultrafiltration, e.g., during hemodiafiltration, by which differences in fluid pressure bring about filtration of a protein-free fluid from the blood. Hemodialysis includes acute hemodialysis and maintenance hemodialysis.

Maintenance hemodialysis refers to long-term hemodialysis therapy for treatment of end stage renal failure. Patients on maintenance hemodialysis have been estimated to lose about 2 to 3 grams of iron per year, corresponding to approximately 6 ml per day (2 liters per year) blood loss from all sources (Eschbach et al. *Ann. Intern Med.* 1977, 87(6): 710-3).

Generally, the ionic composition of the final dialysate solution for hemodialysis is as follows: $Na^+$ 132 mmol/L to 145 mmol/L, $K^+$ 0 mmol/L to 4.0 mmol/L, $Cl^-$ 99 mmol/L to 112 mmol/L, $Ca^{++}$ 2.0 mEq/L to 3.5 mEq/L, $Mg^{+2}$ 0.25 mmol/L to 0.75 mmol/L, dextrose 100 mg/dL to 200 mg/dL, and acetate 4.0 mEq/L to 9.0 mEq/L or citrate 2.0 to 5.0 mEq/L. In "Bicarbonate dialysis" the dialysate contains 27 mmol/L to 41 mmol/L of bicarbonate. On the other hand, in "Acetate dialysis" the dialysate is devoid of bicarbonate and contains 31 mmol/L to 45 mmol/L of acetate. In one aspect, a solid particulate formulation comprising SFP of the present disclosure is compatible with both acetate or citrate and bicarbonate based hemodialysis solutions. In another aspect, a solid particulate formulation comprising SFP of the present disclosure is compatible with only a bicarbonate based hemodialysis solution.

Solid Particulate Formulations

The term "particulate formulation" refers to a formulation comprising a population of solid separate particles, optionally in a mixture of sizes, and includes both powder formulations and granular formulations. The term "powder formulation" refers to a dry mixture of solid particles comprising primary particles having a size range (e.g., diameter) of about 1 µm to about 10 µm, for example, about 1 µm to about 4 µm, about 3 µm to about 5 µm, about 2 µm to about 6 µm, about 5 µm to about 10 µm, about 1 µm to about 5 µm, about 3 µm to about 4 µm, or about 1 µm, about 2 µm, about 3 µm, about 4 µm, about 5 µm, about 6 µm, about 7 µm, about 8 µm, about 9 µm, or about 10 µm. In some aspects, a powder formulation comprises primary particles, aggregates of primary particles (e.g., loose and/or durable aggregates), or combinations thereof. Particle size can be determined using methods known in the art, e.g., analytical sieving as described in U.S. Pharmacopeia 29 (USP29), Chapter 786.

The term "granule formulation" refers to a dry mixture of solid particles comprising particles having a size range of about 10 µm to about 50 µm, for example, about 12 µm to about 40 µm, about 15 µm to about 45 µm, about 10 µm to about 40 µm, about 12 µm to about 50 µm, about 20 µm to about 40 µm, or about 10 µm, about 20 µm, about 30 µm, about 40 µm, or about 50 µm. A granule formulation may comprise aggregates of powders. Aggregates may be formed using a wet granulation or dry granulation process.

The terms "flowability" and "powder flow" are used interchangeably and refer to the movement of a solid particulate formulation relative to an apparatus under a specific set of conditions. Powder flow can be affected by the pressure on the powder, the environmental conditions (e.g., temperature, humidity), and the testing equipment. Higher flowability or more rapid powder flow indicate a more free-flowing formulation.

The term "chelate" refers to a metal cation and anions that surround the metal cation and are joined to it by electrostatic bonds, for example, a ferric iron cation surrounded by and joined by electrostatic bonds to both citrate and pyrophosphate anions.

The term "sachet" refers to a package, e.g., a bag, pouch, or packet, containing a solid particulate formulation. A sachet may be made from any of a number of materials, including paper, plastic, foil, and combinations thereof.

SFP Compositions

SFP is an iron preparation of uncertain composition. No definite formula for its constitution is known. The term "SFP" refers to a compositions comprising a mixture of ferric pyrophosphate and other salts that has been rendered soluble. For example, SFP is mixture of ferric pyrophosphate and sodium citrate and SFP is a mixture of four salts (ferric and sodium pyrophosphates and ferric and sodium citrates)" or SPFP is "ferric pyrophosphate that has been rendered soluble by sodium citrate."

In the art, one type of SFP is known as "conventional SFP". Conventional SFP is known to have the properties described in Table 1.

TABLE 1

Properties of Conventional SFP

| Parameter | Observation |
|---|---|
| Chemical Name | 1,2,3-Propanetricarboxylic acid, 2-hydroxy-, iron(3+) sodium salt (1:1:1), mixture with iron(3+) diphosphate |
| CAS Registry No. | 1332-96-3 |
| Appearance | Solid (may be plates, powder, or pearls, depending on the manufacturer) |
| Color | Yellow-green to green |
| Iron Content | 10.5% to 12.5% |
| Solubility in water | Exceeds 1 gram per mL |
| pH of a 5% solution | 5-7 |

Conventional SFP may be obtained commercially. An example of conventional SFP is food grade SFP (FCC-SFP). Analysis of FCC-SFP samples has shown that typical preparations contain iron, pyrophosphate anion, citrate anion, phosphate anion, sulfate anion, and sodium (Table 2).

TABLE 2

Composition of food grade SFP (FCC-SFP)

| | Weight Percent Composition on the Dried Basis | | | | | |
|---|---|---|---|---|---|---|
| Sample No. | A | B | C | D | E | F |
| Iron | 11.8 | 11.4 | 11.9 | 11.1 | 12.0 | 12.0 |
| Pyrophosphate | 10.1 | 8.3 | 4.7 | 9.1 | 9.2 | 10.1 |
| Citrate | 34.3 | 35.9 | 44.2 | 37.6 | 35.8 | 36.5 |
| Phosphate | 16.8 | 17.1 | 12.9 | 15.8 | 17.4 | 16.3 |
| Sodium | 16.0 | 16.1 | 16.6 | 16.2 | 16.4 | 16.2 |
| Sulfate | 12.6 | 16.4 | 15.9 | 19.5 | 14.6 | 4.2 |

Another example of SFP is the composition is the chelate composition described in U.S. Pat. Nos. 7,816,404 and 8,178,709. The SFP may be a ferric pyrophosphate citrate (FPC) comprising a mixed-ligand iron compound comprising iron chelated with citrate and pyrophosphate, optionally FPC has the following formula: $Fe_4(C_6H_4O_7)_3(H_2P_2O_7)_2(P_2O_7)$ (relative MW 1313 daltons), e.g., structure (I):

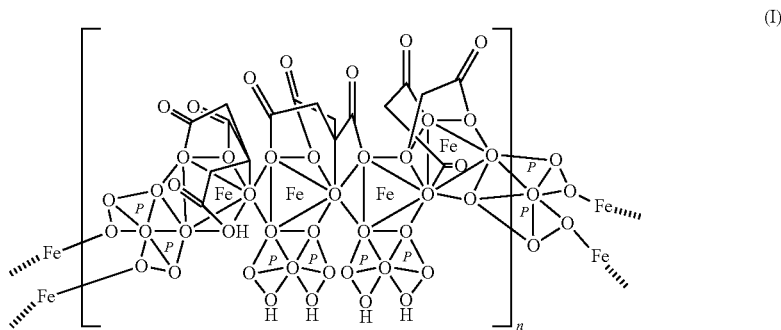

(I)

An exemplary SFP according to the present disclosure is known to have the properties described in Table 3.

TABLE 3

Properties of SFP according to the present disclosure

| Parameter | Observation |
|---|---|
| Chemical Name | Ferric pyrophosphate citrate |
| Molecular formula | $Fe_4(C_6H_4O_7)_3(H_2P_2O_7)_2(P_2O_7)$ |
| Molecular weight | About 1000 Da |
| Fe(III)-ligand binding | Covalent and stable in aqueous solution |
| Appearance | Yellow to Green Powder |
| Transfer across hemodialyzer membrane | Dialyzable, dialysance similar to B12, crosses dialyzer membrane in the form of a mixed ligand iron compound |
| Pharmacologic action | Binds directly to apotransferrin and monoferric transferrin |
| Iron Content | 7.5-9.0% w/w |
| Solubility in water | Exceeds 1 gram per mL |

The present disclosure provides a solid particulate formulation of SFP comprising SFP having a primary particle size less than about 5 μm. For example, the SFP can have a particle size of about 5 μm, about 4.5 μm, about 4 μm, about 3.5 μm, about 3 μm, about 2.5 μm, about 2 μm, about 1.5 μm, about 1 μm, or about 0.5 μm. A solid particulate formulation of SFP according to the disclosure can be prepared by first forming SFP, e.g., as described in U.S. Pat. Nos. 7,816,404 and 8,178,709. Briefly, citrate and pyrophosphate ions are combined in water, ferric ion is added, and water-soluble SFP is isolated, e.g., by drying. The desired particle size of the solid particulate formulation may be achieved by using milling techniques and equipment, including, but not limited to, hammer mills, screen mills, pin mills, spiral jet mills, loop jet mills, and fluidized bed jet mills. In one aspect, the solid particulate formulation has a median particle size less than about 15 μm, for example, about 15 μm, about 14 μm, about 13 μm, about 12 μm, about 11 μm, or about 10 μm. In another aspect, the solid particulate formulation is a granule formulation wherein 90% of the particles have a particle size between about 1 μm and about 50 μm, for example, between about 5 μm and about 50 μm, between about 3 μm and about 40 μm, between about 10 μm and about 30 μm, or between about 1 μm and about 25 μm. The particles in the granule formulation may be obtained by using an appropriate milling technique to produce larger particles, or by forming aggregates of powders, for example, by compressing or otherwise agglomerating powder particles. The SFP exhibits rapid and complete dissolution in an aqueous solution, such as dialysate, dissolving in aqueous solution in less than about one minute. The SFP according to the present disclosure has a crystal structure distinct from FCC-SFP and improved properties including increased aqueous solubility, increased flowability, and faster iron transfer kinetics.

In one aspect, a solid particulate formulation of SFP according to the disclosure is a ferric pyrophosphate citrate (FPC) comprising any SFP composition described herein. For example, a solid particulate formulation of the invention comprises a mixed-ligand iron compound comprising iron chelated with citrate and pyrophosphate, optionally FPC has the following formula: $Fe_4(C_6H_4O_7)_3(H_2P_2O_7)_2(P_2O_7)$ (relative MW 1313 daltons), e.g., structure (I).

In one aspect, a solid particulate formulation of SFP according to the disclosure comprises $Fe^{+3}$ bound to O as the nearest neighbor (2.00 Å) in the primary coordination shell and P (3.20 Å) and C (2.98 Å) as the next-nearest neighbors in secondary coordination, as determined by X-ray Absorption Fine Structure spectroscopy (EXAFS) and shown below in structure (II) (dotted lines represent first and second coordination shells):

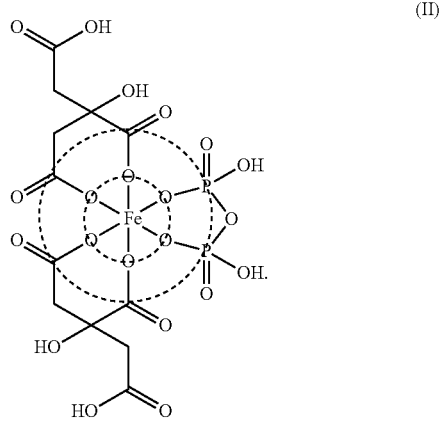

(II)

In one aspect, a solid particulate formulation of SFP according to the disclosure comprises a ferric ion covalently bound with one pyrophosphate molecule and two citrate molecules, wherein the coordination environment of iron in the SFP-iron chelate is the same as solid state structure and remains stable for at least months, indicating greater thermodynamic stability, in aqueous solution. For example, in one aspect, the carbonyl stretching peak of citrate is shifted from 1592 $cm^{-1}$ in sodium citrate to 1610 $cm^{-1}$ and the P=O and P—O stretching bands of pyrophosphate are similarly shifted strongly, as measured using IR spectroscopy.

In one aspect, a solid particulate formulation of SFP according to the disclosure comprises iron in an amount of 7% to 11% by weight, citrate in an amount of at least 14% by weight, and pyrophosphate in an amount of at least 10% by weight. For example, in one aspect, a solid particulate formulation of SFP comprises iron in an amount from 7.5-9.0% by weight, citrate in an amount from 15-22% by weight, pyrophosphate in an amount from 15-22% by weight, phosphate in an amount less than 2%, sodium in an amount from 18-25% by weight, and sulfate in an amount from 20-35% by weight. In another aspect, a solid particulate formulation of SFP according to the disclosure comprises iron in an amount of 9% to 14% by weight, citrate in an amount of 30% to 60% by weight, and pyrophosphate in an amount of 5% to 20% by weight.

In one aspect, the SFP according to the present disclosure exhibits significantly higher water solubility compared to FCC-SFP and has a solubility in aqueous solution greater than 1 g per mL.

In one aspect, a solid particulate formulation of the present disclosure comprises SFP having a high flowability, e.g., as measured in seconds per grams. In one aspect, the SFP has improved flowability compared to FCC-SFP, for example, an improvement of at least about 10%, at least about 20%, at least about 30%, at least about 40%, or more. Methods of characterizing powder flow are known in the art (see, e.g., USP29, Chapter 1174 and European Pharmacopoeia 8$^{th}$ Edition, Chapter 2.9.36, incorporated herein by reference). Commonly used methods include measurement of the angle of repose, compressibility (Carr) index, Hausner ratio, and/or flow rate through an orifice. Additional methods of analyzing powder flow include determination of cohesivity or avalanching, dielectric imaging, atomic force microscopy, penetrometry, and shear cell (see, e.g., Shah et al., AAPS PharmSciTech, 2008, 9(1): 250-258).

The angle of repose is related to resistance to movement between particles (interparticulate friction) and is the constant, three-dimensional angle relative to the horizontal base assumed by a cone-shaped pile of powder. In a typical assay, a symmetrical cone-shaped pile of powder is built by passing a solid particulate formulation through a funnel onto a vibration-free fixed base. The height of the funnel is maintained approximately 2 cm to 4 cm above the pile to minimize the effect of falling particles on the top of the pile. The angle of repose can then be determined by measuring the height and radius of the cone and calculating the angle of repose from the following equation: angle of repose= $tan^{-1}$(height/radius).

In one aspect, the SFP in the solid particulate formulation of the present disclosure has an angle of repose less than about 45 degrees, optionally less than about 42 degrees. For example, the SFP may have an angle of repose between about 41 degrees and 45 degrees. In one aspect, the SFP has an angle of repose of about 41 degrees.

In one aspect, the SFP in the solid particulate formulation of the present disclosure exhibits significantly faster iron transfer kinetics to apotransferrin compared to FCC-SFP. The fast binding kinetics allow $Fe^{3+}$ to be sequestered by transferrin for transport in the blood to the bone marrow for hemoglobin synthesis in a physiological manner, while minimizing the release of labile and non-transferrin bound iron.

A solid particulate formulation of SFP according to the disclosure may optionally comprise one or more pharmaceutically acceptable excipients. Examples of excipients include, but are not limited to, saccharides (mono-, di-, oligo-, poly-, etc.), alcohols, bulking agents, carriers, disintegrants, diluents, binders, preservatives, salts, additives to improve flowability, and mixtures thereof. The excipient(s) may be combined with the SFP in the solid particulate formulation using any conventional technique, optionally using a blender or mixer, e.g., a V-blender, bin blender, static/dynamic continuous blender, planetary blender, high intensity mixer, drum mixer, or tumble mixer.

In one aspect, the present disclosure provides kits comprising a solid particulate formulation of SFP and a dialysis concentrate formulation. In one aspect, the dialysis concentrate formulation is a solid form. For example, a dialysis concentrate formulation in solid form may comprise 100% sodium bicarbonate or 73.7% sodium bicarbonate and 26.3% sodium chloride. In another aspect, the dialysis concentrate formulation is a liquid form. For example, a dialysis concentrate formulation in liquid form may comprise 60-70 w/v % water, 19-21 w/v % sodium chloride, up to 0.5 w/v % potassium chloride, up to 0.6 w/v % calcium chloride, 0.2-0.3 w/v % magnesium chloride, up to 7 w/v % dextrose, and 10.3-10.9 w/v % sodium acetate. In another example, a dialysis concentrate formulation in liquid form may comprise 8% sodium bicarbonate in water or 6.6% sodium bicarbonate and 2.3% sodium chloride in water. The dialysis concentrate formulation may be an acid or base. For example, an acid dialysis concentrate formulation in a solid or liquid form may comprise 75-80 w/v % water, 17-26 w/v % sodium chloride, up to 1.3 w/v % potassium chloride, up to 1.0 w/v % calcium chloride, 0.1-0.6 w/v % magnesium chloride, up to 10 w/v % dextrose, and 0.6-0.7% citric acid. In another example, an acid dialysis concentrate formulation in solid or liquid form may comprise 75-80 w/v % water, 17-26 w/v % sodium chloride, up to 1.3 w/v % potassium chloride, up to 1.0 w/v % calcium chloride, 0.2-0.6 w/v % magnesium chloride, up to 10 w/v % dextrose, and 0.6-0.7 w/v % acetic acid. Dialysate may be prepared from a dialysis concentrate formulation using a mixing system, e.g., as described in U.S. Pat. No. 6,395,180, incorporated herein by reference. In one aspect, the solid particulate formulation of SFP in the kit is a powder formulation. In another aspect, the solid particulate formulation of SFP in the kit is a granule formulation. In one aspect, the kit includes written instructions for mixing the solid particulate formulation of SFP with the dialysis concentrate formulation, and optionally diluting the mixture with water to form a dialysis solution to be administered to a patient.

Solid particulate formulations of SFP of the present disclosure may be stored in packages of various types. For example, a solid particulate formulation may be stored in a capsule that is broken, a blister pack that is pierced or peeled, or a sachet that are opened, to allow for the solid particulate formulation contained therein to be added to an aqueous solution, e.g., a dialysis concentrate formulation. Optionally, the solid particulate formulation is formed into a single mass, e.g., a tablet or wafer, that can be added directly to an aqueous solution, or the solid particulate formulation is stored within a dissolvable package that is soluble in an aqueous solution.

In one aspect, the present disclosure provides a sachet, e.g., a packet, comprising a solid particulate formulation described herein, optionally in a kit. In one aspect, the sachet comprises a dose or multiple doses of SFP to be added to a dialysis solution to form a dialysate, optionally to result in a final iron concentration of about 110 mcg/L (about 2 μM) in the dialysate to be administered to a patient e.g., during hemodialysis or hemodiafiltration. In another aspect, the sachet comprises a dose or multiple doses of SFP that will be added to an intravenous solution [to form an intravenous fluid with a final iron concentration of 1 mg per liter to 1 mg per mL, to be administered to a patient via intravenous injection or infusion. In another aspect, the sachet comprises a dose of SFP that can be mixed with food or drink to provide a nutritional supplement. Table 4 shows the amount of iron derived from SFP present in a sachet according to the present disclosure and the corresponding volume of a bicarbonate dialysis concentrate formulation for mixing with the contents of the sachet.

TABLE 4

Sachet Compositions

SFP-Derived Iron (mg)

| | Bicarbonate Concentrate (gallons) |
|---|---|
| 10.88 | 1 |
| 27.2 | 2.5 |
| 54.4 | 5 |
| 272.0 | 25 |
| 544.0 | 50 |
| 1088.0 | 100 |
| | Bicarbonate Concentrate (liters) |
| 2.878 | 1 |
| 14.39 | 5 |
| 28.78 | 10 |
| 71.95 | 25 |
| 143.9 | 50 |
| 287.8 | 100 |
| 575.6 | 200 |
| 1439.0 | 500 |

The present disclosure provides an improved method of administering SFP comprising (a) mixing a solid particulate formulation of SFP with a dialysis solution to form a dialysate and (b) administering the dialysate to a subject in need. In one aspect, the dialysis solution is an acid solution. In one aspect, the acid solution comprises citrate. In a further aspect, the solubility of the solid particulate formulation in the acid solution is greater than 1 g/mL. In another aspect, the dialysis solution is a base solution. In one aspect, the base solution comprises bicarbonate. In a further aspect, the solubility of the solid particulate formulation in the base solution is greater than 1 g/mL. In one aspect, the mixing of the solid particulate formulation of SFP with the dialysis solution results in an iron concentration of about 100 μg/L to about 150 μg/L in the dialysate, for example, about 110 μg/L or about 2 μM.

In one aspect, the improved method of administering SFP comprises administering a solid particulate formulation of SFP comprising iron chelated with citrate and pyrophosphate, for example, iron (III) covalently bound to pyrophosphate and citrate. U.S. Pat. Nos. 7,816,404 and 8,178,709, incorporated herein by reference, discloses methods of preparing SFP-citrate chelate compositions in accordance with GMP standards and the present disclosure. In one aspect, the improved method of administering SFP comprises a solid particulate formulation of SFP comprising iron in an amount of 7% to 11% by weight, citrate in an amount of at least 14% by weight, and pyrophosphate in an amount of at least 10% by weight, for example, iron in an amount from 7.5-9.0% by weight, citrate in an amount from 15-22% by weight, and pyrophosphate in an amount from 15-22% by weight, optionally further comprising phosphate in an amount less than 2%, sodium in an amount from 18-25% by weight, and sulfate in an amount from 20-35% by weight. In another aspect, the improved method of administering SFP comprising a solid particulate formulation of SFP comprising iron in an amount of 9% to 14% by weight, citrate in an amount of 30% to 60% by weight, and pyrophosphate in an amount of 5% to 20% by weight, optionally further comprising sodium in an amount from 1% to 15% by weight, and essentially no sulfate. In another aspect, the improved method of administering SFP comprises a solid particulate formulation of SFP comprising iron chelated with citrate and pyrophosphate, for example, FPC having the following formula: $Fe_4(C_6H_4O_7)_3(H_2P_2O_7)_2(P_2O_7)$ (relative MW 1313 daltons, e.g., structure (I).

In one aspect, the dose of SFP for any of the preceding methods is administered via dialysate at an iron dose ranging from 90 µg/L dialysate to 150 µg/L dialysate, or at a dose ranging from 90 µg/L dialysate to 140 µg/L dialysate, or at a dose ranging from 90 µg/L dialysate to 130 µg/L dialysate, or at a dose ranging from 90 µg/L dialysate to 120 µg/L dialysate, or at a dose ranging from 90 µg/L dialysate to 110 µg/L dialysate, or at a dose ranging from 90 µg/L dialysate to 105 µg/L dialysate, or at a dose ranging from 105 µg/L dialysate to 115 µg/L dialysate, or at a dose ranging from 105 µg/L dialysate to 110 µg/L dialysate, or at a dose ranging from 105 µg/L dialysate to 120 µg/L dialysate, or at a dose ranging from 105 µg/L dialysate to 130 µg/L dialysate, or at a dose ranging from 105 µg/L dialysate to 140 µg/L dialysate, or at a dose ranging from 105 µg/L dialysate to 150 µg/L dialysate, or at a dose ranging from 110 µg/L dialysate to 150 µg/L dialysate, or at a dose ranging from 110 µg/L dialysate to 140 µg/L dialysate, or at a dose ranging from 110 µg/L dialysate to 130 µg/L dialysate, or at a dose ranging from 110 µg/L dialysate to 120 µg/L dialysate, or at a dose ranging from 110 µg/L dialysate to 115 µg/L dialysate, or at a dose ranging from 112 µg/L dialysate to 150 µg/L dialysate, or at a dose ranging from 112 µg/L dialysate to 140 µg/L dialysate, or at a dose ranging from 112 µg/L dialysate to 130 µg/L dialysate, or at a dose ranging from 112 µg/L dialysate to 120 µg/L dialysate, or at a dose ranging from 112 µg/L dialysate to 118 µg/L dialysate, or at a dose ranging from 112 µg/L dialysate to 115 µg/L dialysate, or at a dose ranging from 115 µg/L dialysate to 150 µg/L dialysate, or at a dose ranging from 115 µg/L dialysate to 140 µg/L dialysate, or at a dose ranging from 115 µg/L dialysate to 130 µg/L dialysate, or at a dose ranging from 115 µg/L dialysate to 120 µg/L dialysate, or at a dose ranging from 120 µg/L dialysate to 150 µg/L dialysate, or at a dose ranging from 120 µg/L dialysate to 140 µg/L dialysate, or at a dose ranging from 120 µg/L dialysate to 130 µg/L dialysate, or at a dose ranging from 120 µg/L dialysate to 125 µg/L dialysate, or at a dose ranging from 130 µg/L dialysate to 150 µg/L dialysate, or at a dose ranging from 130 µg/L dialysate to 140 µg/L dialysate, or at a dose ranging from 140 µg/L dialysate to 150 µg/L dialysate.

In an exemplary aspect, the dose of SFP is administered at a dose of 110 µg or 2 moles SFP-iron per liter of hemodialysate. In addition, the invention provides for methods wherein the dose of SFP iron is administered via dialysate at a dose of about 105 µg/L dialysate, about 106 µg/L dialysate, about 107 µg/L dialysate, about 108 µg/L dialysate, about 109 µg/L dialysate, about 110 µg/L dialysate, about 111 µg/L dialysate or about 112 µg/L dialysate.

In one aspect, the SFP crosses the dialyzer membrane from the hemodialysate to the blood compartment and the SFP-derived Fe(III) binds rapidly to apotransferrin, for example, to the N-lobe in conjunction with pyrophosphate and to the C lobe in conjunction with carbonate. In various aspects, the SFP raises serum ion levels, decreases unsaturated iron binding capacity (UIBC) of plasma by direct binding of SPF-iron to apotransferrin and monoferric transferrin, and/or maintains reticulocyte hemoglobin and whole blood hemoglobin, demonstrating that SFP-derived iron is delivered to the erythron for hemoglobin generation and erythropoiesis. When SFP is administered according to the disclosure, the direct iron transfer from SFP to iron binding sites on plasma apotransferrin mimics the physiological handling of dietary iron after absorption, which is a unique mode of action distinct from the mode of action of iron-carbohydrate complexes currently approved for intravenous administration, which are typically nanoparticles that are removed from the circulation, stored, and processed by macrophages prior to release of iron in the circulation for binding to apotransferrin.

In one aspect, the dose of SFP for any of the preceding methods is administered via infusion at a dose ranging from 2.4 mg to 48 mg per day at a rate of 0.1 to 2 mg per hour. In another aspect, the dose of SFP is administered via intravenous injection at a dose ranging from 2.4 mg to 48 mg per day at a rate of 0.1 to 2 mg per hour. In addition, the present disclosure provides for any of the preceding methods wherein, the dose of SFP is administered into the circulation at a dose ranging from 2.4 mg to 48 mg per day at a rate of 0.1 to 2 mg per hour. For any of these methods, the dose administered to the subject is based on the bioavailability of SFP using the specific route of administration.

Additional exemplary dose ranges for administering SFP-iron via infusion, intravenous injection or delivery into the circulation include a dose ranging from 5 mg to 48 mg per day at a rate of 0.1 to 2 mg per hour, or at a dose ranging from 10 mg to 48 mg per day at a rate of 0.01 to 2 mg per hour, or at a dose ranging from 20 mg to 48 mg per day at a rate of 0.01 to 2 mg per hour, or at a dose ranging from 30 mg to 48 mg per day at a rate of 0.01 to 2 mg per hour, or at a dose ranging from 40 mg to 48 mg per day at a rate of 0.01 to 2 mg per hour, or a dose ranging from 2.4 mg to 48 mg per day at a rate of 1 to 2 mg per hour, or a dose ranging from 5 mg to 48 mg per day at a rate of 1 to 2 mg per hour, or at a dose ranging from 10 mg to 48 mg per day at a rate of 1 to 2 mg per hour, or at a dose ranging from 20 mg to 48 mg per day at a rate of 1 to 2 mg per hour, or at a dose ranging from 30 mg to 48 mg per day at a rate of 1 to 2 mg per hour, or at a dose ranging from 40 mg to 48 mg per day at a rate of 1 to 2 mg per hour, or a dose ranging from 2.4 mg to 48 mg per day at a rate of 0.5 to 1 mg per hour, or a dose ranging from 5 mg to 48 mg per day at a rate of 0.5 to 1 mg per hour, or at a dose ranging from 10 mg to 48 mg per day at a rate of 0.5 to 1 mg per hour, or at a dose ranging from 20 mg to 48 mg per day at a rate of 0.5 to 1 mg per hour, or at a dose ranging from 30 mg to 48 mg per day at a rate of 0.5 to 1 mg per hour, or at a dose ranging from 40 mg to 48 mg per day at a rate of 0.5 to 1 mg per hour, a dose ranging from 2.4 mg to 40 mg per day at a rate of 0.1 to 2 mg per hour, or a dose ranging from 5 mg to 40 mg per day at a rate of 0.1 to 2 mg per hour, or at a dose ranging from 10 mg to 40 mg per day at a rate of 0.01 to 2 mg per hour, or at a dose ranging from 20 mg to 40 mg per day at a rate of 0.01 to 2 mg per hour, or at a dose ranging from 30 mg to 40 mg per day at a rate of 0.01 to 2 mg per hour, or at a dose ranging from 40 mg to 40 mg per day at a rate of 0.01 to 2 mg per hour, or a dose ranging from 2.4 mg to 40 mg per day at a rate of 1 to 2 mg per hour, or a dose ranging from 5 mg to 40 mg per day at a rate of 1 to 2 mg per hour, or at a dose ranging from 10 mg to 40 mg per day at a rate of 1 to 2 mg per hour, or at a dose ranging from 20 mg to 40 mg per day at a rate of 1 to 2 mg per hour, or at a dose ranging from 30 mg to 40 mg per day at a rate of 1 to 2 mg per hour, a dose ranging from 2.4 mg to 40 mg per day at a rate of 0.5 to 1 mg per hour, or a dose ranging from 5 mg to 40 mg per day at a rate of 0.5 to 1 mg per hour, or at a dose ranging from 10 mg to 40 mg per day at a rate of 0.5 to 1 mg per hour, or at a dose ranging from 20 mg to 40 mg per day at a rate of 0.5 to 1 mg per hour, or at a dose ranging from 30 mg to 40 mg per day at a rate of 0.5 to 1 mg per hour, a dose ranging from 2.4 mg to 30 mg per day at a rate of 0.1 to 2 mg per hour, or a dose ranging from 5 mg to 30 mg per day at a rate of 0.1 to 2 mg per hour, or at a dose ranging from 10 mg to 30 mg per day at a rate of 0.01 to 2 mg per hour, or at a dose ranging from 20 mg to 30 mg per day at a rate of 0.01 to 2 mg per hour, or a dose ranging from 2.4 mg to 30 mg per day at a rate of 1 to 2 mg per hour, or a dose ranging from 5 mg to 30 mg per day at a rate of 1 to 2 mg per hour, or at a dose ranging from 10 mg to 30 mg per day at a rate of 1 to 2 mg per hour, or at a dose ranging from 20 mg to 30 mg per day at a rate of 1 to 2 mg per hour, a dose ranging from 2.4 mg to 30 mg per day at a rate of 0.5 to 1 mg per hour, or a dose ranging from 5 mg to 30 mg per day at a rate of 0.5 to 1 mg per hour, or at a dose ranging from 10 mg to 30 mg per day at a rate of 0.5 to 1 mg per hour, or at a dose ranging from 20 mg to 30 mg per day at a rate of 0.5 to 1 mg per hour, a dose ranging from 2.4 mg to 20 mg per day at a rate of 0.1 to 2 mg per hour, or a dose ranging from 5 mg to 20 mg per day at a rate of 0.1 to 2 mg per hour, or at a dose ranging from 10 mg to 20 mg per day at a rate of 0.01 to 2 mg per hour, or a dose ranging from 2.4 mg to 20 mg per day at a rate of 1 to 2 mg per hour, or a dose ranging from 5 mg to 20 mg per day at a rate of 1 to 2 mg per hour, or at a dose ranging from 10 mg to 20 mg per day at a rate of 1 to 2 mg per hour, a dose ranging from 2.4 mg to 20 mg per day at a rate of 0.5 to 1 mg per hour, or a dose ranging from 5 mg to 20 mg per day at a rate of 0.5 to 1 mg per hour, or at a dose ranging from 10 mg to 20 mg per day at a rate of 0.5 to 1 mg per hour, a dose ranging from 5 mg to 10 mg per day at a rate of 0.1 to 2 mg per hour, a dose ranging from 5 mg to 10 mg per day at a rate of 0.1 to 2 mg per hour, or a dose ranging from 2.4 mg to 10 mg per day at a rate of 1 to 2 mg per hour, or a dose ranging from 5 mg to 10 mg per day at a rate of 1 to 2 mg per hour, or a dose ranging from 2.4 mg to 10 mg per day at a rate of 0.5 to 1 mg per hour, a dose ranging from 5 mg to 10 mg per day at a rate of 0.5 to 1 mg per hour, or a dose ranging from 2.4 mg to 5 mg per day at a rate of 0.1 to 2 mg per hour, or a dose ranging from 2.4 mg to 5 mg per day at a rate of 0.5 to 1 mg per hour, a dose ranging from 2.4 mg to 5 mg per day at a rate of 1 to 2 mg per hour.

The methods of the invention may be used to treat a subject in need. The invention also provides for using the solid particulate formulation of SFP comprising iron chelated with citrate and pyrophosphate for the preparation of a medicament to treat a subject in need, and provides for compositions comprising the solid particulate formulation of SFP comprising iron chelated with citrate and pyrophosphate for the use in treating a subject in need. Suitable subjects are those that would benefit from iron supplementation, including subjects suffering from iron deficiency including anemia and/or subjects undergoing dialysis or diafiltration. Anemia is a condition when the number of red blood cells and/or the amount of Hgb found in the red blood cells is below normal, and may be acute or chronic. Examples of anemia that may be treated using the formulations, kits, and methods of the present disclosure include, but are not limited to, iron deficiency anemia, renal anemia, anemia of chronic diseases/inflammation, cancer-related anemia, chemotherapy-related anemia, anemia caused by impaired production of ESA, hypochromic anemia, and microcytic anemia. Anemia may cause serious symptoms, including hypoxia, chronic fatigue, lack of concentration, pale skin, low blood pressure, dizziness and heart failure.

In any of the preceding methods, uses, or compositions of the present disclosure, the subject may be suffering from chronic kidney disease (CKD), optionally stage II, III, IV or V.

In addition, the present disclosure provides for any of the preceding methods, uses, or compositions, wherein the subject is undergoing hemodialysis or hemodiafiltration. In one aspect, the subject is a CKD patient on hemodialysis (e.g., having HDD-CKD) with iron-restricted erythropoiesis. In one aspect, the method comprises administering small regular doses of SFP to replace concurrent CKD and hemodialysis related iron losses to maintain the iron balance in a subject having inadequate iron stores.

The present disclosure also provides for any of the preceding methods, uses, or compositions, wherein the subject is suffering from anemia of inflammation.

The present disclosure also provides for any of the preceding methods, uses, or compositions, wherein the subject is suffering from infection, optionally chronic infection.

Furthermore, the present disclosure provides for any of the preceding methods, uses, or compositions, wherein the subject is suffering from cancer, heart failure, autoimmune disease, sickle cell disease, thalassemia, blood loss, transfusion reaction, diabetes, vitamin B12 deficiency, collagen vascular disease, Shwachman syndrome, thrombocytopenic purpura, Celiac disease, endocrine deficiency state such as hypothyroidism or Addison's disease, autoimmune disease such as Crohn's Disease, systemic lupus erythematosis, rheumatoid arthritis or juvenile rheumatoid arthritis, ulcerative colitis immune disorders such as eosinophilic fasciitis, hypoimmunoglobulinemia, or thymoma/thymic carcinoma, graft vs. host disease, preleukemia, Nonhematologic syndrome (Down's, Dubowwitz, Seckel), Felty syndrome, hemolytic uremic syndrome, myelodysplastic syndrome, nocturnal paroxysmal hemoglobinuria, osteomyelofibrosis, pancytopenia, pure red-cell aplasia, Schoenlein-Henoch purpura, malaria, protein starvation, menorrhagia, systemic sclerosis, liver cirrhosis, hypometabolic states, congestive heart failure, chronic infections such as HIV/AIDS, tuberculosis, oseomyelitis, hepatitis B, hepatitis C, Epstein-bar virus or parvovirus, T cell leukemia virus, bacterial overgrowth syndrome, fungal or parasitic infections, and/or red cell membrane disorders such as hereditary spherocytosis, hereditary elliptocytosis, hereditary pyrpoikilocytosis, hereditary stomatocytosis, red cell enzyme defects, hypersplenism, immune hemolysis or paroxysmal nocturnal hemoglobinuria.

In addition, the present disclosure provides for any of the preceding methods, uses, or compositions, wherein the anemia is due to overt iron deficiency with depleted iron stores or a functional iron deficiency.

The present disclosure provides for any of the preceding methods, uses, or compositions, wherein SFP is administered during hemodialysis or hemodiafiltration within the hemodialysate solution. In addition, the present disclosure provides for any of the preceding methods wherein SFP is administered with oral or parenteral (e.g., intravenous injection or infusion) nutrition within a nutrition admixture.

The invention also provides for any of the preceding methods, uses, or compositions, wherein SFP is administered at a therapeutically effective dose that i) increases at least one marker of iron status selected from the group consisting of serum iron, transferrin saturation, reticulocyte hemoglobin, serum ferritin, reticulocyte count, and whole blood hemoglobin and ii) decreases or eliminates the need for ESA administration to achieve or maintain target hemoglobin levels, or the need for transfusion of whole blood, packed red blood cell or blood substitutes. In addition, when any of the preceding methods are carried out in a subject is suffering from non-anemic iron deficiency and administration of the therapeutically effective dose of SFP reduces fatigue, increases physical and cognitive ability, or improves exercise tolerance in the subject.

In addition, the present disclosure provides for any of the preceding methods, uses, or compositions wherein SFP is administered in a therapeutically effective dose that will reduce or abolish the clinical manifestations of restless leg syndrome associated with iron deficiency.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

The present disclosure will be more readily understood by reference to the following Examples, which are provided by way of illustration and are not intended to be limiting.

EXAMPLES

The following Examples describe methods of using the solid particulate formulations. In general, the solid particulate formulations of the present disclosure can be prepared by the methods described in U.S. Pat. Nos. 7,816,404 and 8,178,709, incorporated herein by reference. For therapeutic purposes, the active components of solid particulate formulation may be ordinarily combined with one or more excipients appropriate to the indicated route of administration.

Example 1

Structure Characterization of SFP

A solid particulate formulation of SFP comprising iron chelated with citrate and pyrophosphate (FPC having structure (I)) was prepared as described above. Structural characterization of the compounds was carried out using Fe K edge X-ray Absorption Near Edge Structure (XANES) and Extended X-Ray Absorption Fine Structure (EXAFS) spectroscopy to ascertain differences in the coordination environment of Fe in a solid particulate formulation of the present disclosure compared to FCC-SFP. Linear combination fitting of Fe XANES data showed that Iron was in the ferric ($Fe^{3+}$) state and did not complex with sulfate in the food grade as well as in the solid particulate formulation. There were 6 coordinated oxygen atoms: 4 from citrate and 2 from pyrophosphate. EXAFS analysis demonstrated that Fe complexation with Oxygen (2.02 Å) in the first coordination sphere was similar in both the food grade SFP and the solid particulate formulation. However, significant differences were observed in the coordination environment of Fe with P (3.22 Å) and C (2.98 Å) binding in the second coordination sphere of Fe in the FCC-SFP and SFP of the present disclosure. IR spectroscopy showed that the carbonyl stretching peak of citrate was shifted from 1592 $cm^{-1}$ in sodium citrate to 1610 $cm^{-1}$ in the SFP of the present disclosure. X-ray powder diffraction analysis of the SFP of the present disclosure showed diffuse scattering in the range of angles 1-15° (2θ) indicating an amorphous nature of material that does not lend itself to single crystal growth suitable for structure determination.

Example 2

Flowability Characterization

Angle of repose measurements were performed using a solid particulate formulation of SFP prepared as described in Example 1 according to the basic method as described in USP <1174>. The result was calculated as an average of 3 replicate measurements and is given in Table 5 below.

TABLE 5

Angle of Repose Measurements

| Measurement | Base Diameter (cm) | Height (cm) | Angle of Response (°) |
|---|---|---|---|
| 1 | 11.85 | 5.4 | 42.3 |
| 2 | 10.65 | 4.7 | 41.4 |
| 3 | 10.15 | 4.4 | 40.9 |
|  |  | Average | 41.5 |

Example 3

Particle Size Characterization

Particle morphology of a solid particulate formulation comprising iron chelated with citrate and pyrophosphate prepared as described in Example 1 was examined via light microscopy as dry powder dispersions and dispersions of powder in mineral oil under various objective lenses. The gross visual appearance of the material was a light green cohesive powder. Microscopically, the formulation appeared as loose aggregates and durable agglomerates comprised of primary particles typically>5 μm. The particle size distribution of the formulation was measured via an in-house particle size method using a Cilas 1180LD laser diffraction particle sizer in liquid dispersion mode with mineral oil as the dispersion media. Three replicate measurements were collected and the results are given in Table 6.

TABLE 6

Particle Size Distribution

| Measurement | $D_{10}$ (μm) | $D_{50}$ (μm) | $D_{90}$ (μm) |
|---|---|---|---|
| 1 | 3.57 | 12.73 | 41.08 |
| 2 | 3.63 | 12.66 | 40.18 |
| 3 | 3.68 | 12.58 | 39.23 |

Example 4

Clinical Use

A sachet comprising Paper/7.5#LDPA/0.000285 ga Foil/13#EAA:LDPE (3.0"×2.5") containing SFP in a ferric pyrophosphate citrate complex, as described in Example 1, corresponding to 272 mg iron was prepared. To prepare dialysate, the sachet was opened and its contents were mixed with 25 gallons of bicarbonate concentrate. The mixture was diluted with water to a final iron concentration of 2 μM (110 mcg/L) in the dialysate.

The SPF was administered to patients undergoing hemodialysis, as described in Gupta et al., Kidney Int. 2015 November; 88(5):1187-94, advance online publication 8 Jul. 2015, and Fishbane et al., Nephrol Dial Transplant 2015 Dec.; 30(12):2019-26, advance online publication 13 Jul. 2015, incorporated herein by reference. In two randomized, single blind, placebo-controlled clinical trials, a total of 292 patients were administered the SFP for periods of up to 48 weeks. Patients with hemoglobin of 9.5 g/dL to 11.5 g/dL with TSAT>15% (e.g., 15% to 40%) and serum ferritin concentrations>200 mcg/L (e.g., 200 mcg/L to 800 mcg/L) were enrolled. Patients were to remain in randomized treatment until pre-specified hemoglobin or ferritin criteria were met, indicating the need for a change in anemia management, or if they completed 48 weeks. The mean total exposure in the randomized treatment period was 5 months.

In Study 1, the mean age of patients was 58 years (range 23 to 89); 32% were female, 55% were Caucasian, 32% were African American, and 13% were other races. In Study 2, the mean age of patients was 58 years (range 20 to 89); 41% were female, 54% were Caucasian, 40% were African American, and 6% were other races.

The SFP having a final concentration of 110 mcg iron/L in the dialysate was administered 3 or 4 times per week during hemodialysis. Patients were receiving stable dose of erythropoiesis stimulating agents (ESAs) at baseline, and the ESA doses were not to be changed 6 weeks prior to randomization. The primary endpoint of the studies was the mean change in hemoglobin from baseline to the end-of-treatment period (average hemoglobin of the last one-sixth (1/6th) of the time in the randomized treatment period). Table 7 shows the mean changes in hemoglobin (Hgb) and iron parameters in each treatment group from baseline to the end-of-treatment period for the ITT population.

TABLE 7

Changes from Baseline to End of Treatment in Hemoglobin, Ferritin, Reticulocyte Hgb (CHr), and Transferrin Saturation (TSAT).

|  | Study 1 | | Study 2 | |
| --- | --- | --- | --- | --- |
|  | SFP n = 152 | Placebo n = 153 | SFP n = 147 | Placebo n = 147 |
| Baseline Hemoglobin Mean ± SD, g/dL | 10.96 (0.592) | 10.91 (0.632) | 10.96 (0.605) | 10.94 (0.622) |
| Hemoglobin Change from Baseline to End-of-Treatment Period Mean ± SD g/dL | −0.03 (1.147)† | −0.38 (1.240) | −0.08 (1.152)† | −0.44 (1.157) |
| Baseline Ferritin Mean (SD), mcg/L | 508.2 (193.55) | 509.3 (209.06) | 519.0 (201.56) | 478.4 (200.59) |
| Ferritin, Change from Baseline to End-of-Treatment Mean (SD), mcg/L | −70.8 (132.41) | −141.2 (187.74) | −65.3 (162.45) | −120.9 (268.19) |
| Baseline Reticulocyte Hemoglobin (CHr) Mean (SD), pg | 32.37 (1.967) | 32.53 (1.965) | 32.56 (2.210) | 32.57 (1.932) |
| CHr, Change from Baseline to End-of-Treatment Mean (SD), pg | −0.22 (1.191) | −0.90 (1.407) | −0.55 (1.441) | −0.85 (1.474) |
| Baseline TSAT Mean (SD), % | 28.2 (8.23) | 27.1 (7.76) | 28.0 (8.15) | 28.2 (8.52) |
| TSAT, Change from Baseline to End-of-Treatment) Mean (SD), % | −1.0 (9.07) | −2.9 (7.65) | −0.9 (7.54) | −3.6 (7.29) |

†p < 0.05 for primary efficacy endpoint

The pharmacokinetics of serum iron was investigated in healthy volunteers administered the following doses of SFP according to the disclosure: dose of 2.5, 5, 7.5 and 10 mg SFP were intravenously administered over 4 hours, or dose of 15 mg and 20 mg SFP were administered intravenously over 12 hours. After correcting for the basal iron levels, the AUC and $C_{max}$ of baseline-corrected serum iron increased in a dose proportional manner. The half-life of serum iron was approximately 1.48 hours, the mean clearance (CL) ranged from 0.406 to 0.556 L/hour, the mean apparent volume of distribution (Vz) ranged from 0.765 to 0.859 L after a 4 hour intravenous administration of SFP according to the disclosure. Compared to the 4 hour infusion of SFP, higher mean CL and Vz were observed following the administration of SFP 15 mg (CL=0.672 L/hour and Vz=1.66 L) and SFP 20 mg (CL=0.661 L/hour, Vz=2.08L) infused over 12 hours. In a study that assessed the impact of different dialysis conditions on iron delivery in patients administered SFP via hemodialysis, a reduction of the blood and dialysate flow rates (Qb/Qd of 200/400 mL/min vs.≥350/≥600 mL/min) resulted in a 33% decrease in the median cumulative iron delivered.

Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. A solid particulate formulation of soluble ferric pyrophosphate citrate chelate comprising milled soluble ferric pyrophosphate wherein 90% of the particles have a particle size between 1 μm and 50 μm.

2. The solid particulate formulation of claim 1, wherein the soluble ferric pyrophosphate citrate chelate has an angle of repose less than 45 degrees.

3. The solid particulate formulation of claim 1 that is stable in aqueous solution at ambient temperature for at least 24 months.

4. The solid particulate formulation of claim 1, wherein the soluble ferric pyrophosphate citrate chelate comprises iron in an amount of 7% to 11% by weight, citrate in an amount of at least 14%, and pyrophosphate in an amount of at least 10%.

5. The solid particulate formulation of claim 1, comprising iron in an amount from 7.5-9.0% by weight, citrate in an amount from 15-22% by weight, pyrophosphate in an amount from 15-22% by weight, phosphate in an amount less than 2%, sodium in an amount from 18-25% by weight, and sulfate in an amount from 20-35% by weight.

6. The solid particulate formulation of claim 1, comprising iron in an amount from 9-14% by weight, citrate in an amount from 30-60% by weight, pyrophosphate in an amount from 5-20% by weight, sodium in an amount from 1-15% by weight, and essentially no sulfate.

7. The solid particulate formulation of claim 1, comprising a compound having structure (I):

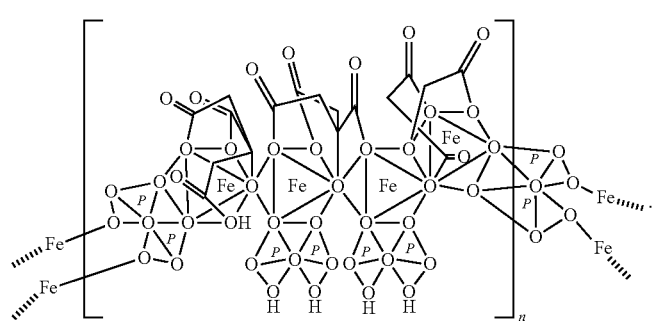

(I)

8. The solid particulate formulation of claim 1, wherein the soluble ferric pyrophosphate citrate chelate has an angle of repose less than 42 degrees.

9. The solid particulate formulation of claim 1, wherein 90% of the particles have a particle size between 3 μm and 40 μm.

10. The solid particulate formulation of claim 1, wherein 90% of the particles have a particle size between 10 μm and 30 μm.

11. The solid particulate formulation of claim 1, wherein 90% of the particles have a particle size between 1 μm and 25 μm.

12. A sachet comprising the solid particulate formulation of claim 1.

13. The sachet of claim 12, comprising a dose of soluble ferric pyrophosphate citrate chelate that will result in a final iron concentration of 110 μg/L or 2 μM in a dialysate to be administered to a patient receiving hemodialysis.

14. A kit comprising the solid particulate formulation of claim 1 and a dialysis concentrate formulation in a solid or liquid form.

15. The kit of claim 14, wherein the dialysis concentrate formulation is a solid form.

16. The kit of claim 14, wherein the dialysis concentrate formulation is a liquid form.

17. The kit of claim 14, wherein the dialysis concentrate formulation is an acid.

18. The kit of claim 14, wherein the dialysis concentrate formulation is a base.

19. A composition comprising particles of a soluble ferric pyrophosphate citrate chelate, comprising 90% of the particles having a particle size between 1 μm and 50 μm.

20. The composition of claim 19, wherein the soluble ferric pyrophosphate citrate chelate has an angle of repose less than 45 degrees.

21. The composition of claim 19, wherein the soluble ferric pyrophosphate citrate chelate has an angle of repose less than 42 degrees.

22. The composition of claim 19, wherein the soluble ferric pyrophosphate citrate chelate comprises iron in an amount of 7% to 11% by weight, citrate in an amount of at least 14%, and pyrophosphate in an amount of at least 10%.

23. The composition of claim 19, comprising iron in an amount from 7.5-9.0% by weight, citrate in an amount from 15-22% by weight, pyrophosphate in an amount from 15-22% by weight, phosphate in an amount less than 2%, sodium in an amount from 18-25% by weight, and sulfate in an amount from 20-35% by weight.

24. The composition of claim 19, comprising iron in an amount from 9-14% by weight, citrate in an amount from 30-60% by weight, pyrophosphate in an amount from 5-20% by weight, sodium in an amount from 1-15% by weight, and essentially no sulfate.

* * * * *